United States Patent [19]

Zardi et al.

[11] 4,314,077

[45] Feb. 2, 1982

[54] METHOD FOR THE PRODUCTION OF UREA AND PURIFICATION OF WATER

[75] Inventors: Umberto Zardi, San Donato Milanese; Vincenzo Lagana', Milan, both of Italy

[73] Assignee: Snamprogetti S.p.A., Milan, Italy

[21] Appl. No.: 216,303

[22] Filed: Dec. 15, 1980

Related U.S. Application Data

[63] Continuation of Ser. No. 91,988, Nov. 7, 1979, abandoned, which is a continuation of Ser. No. 823,872, Aug. 11, 1977, abandoned.

[30] Foreign Application Priority Data

Sep. 9, 1976 [IT] Italy .............................. 27024 A/76

[51] Int. Cl.³ .......................................... C07C 126/02
[52] U.S. Cl. ...................................... 564/70; 564/72
[58] Field of Search ............................ 564/70, 71, 72

[56] References Cited

U.S. PATENT DOCUMENTS

| | | | |
|---|---|---|---|
| 3,120,563 | 2/1964 | Bongard | 260/555 A |
| 3,826,815 | 7/1974 | Mavrovic | 423/356 |
| 3,876,696 | 4/1975 | Guadalupi | 260/555 A |
| 3,922,222 | 11/1975 | Van Moorsel | 210/71 |
| 3,944,605 | 3/1976 | Inoue | 260/555 A |
| 4,012,443 | 3/1977 | Bonetti | 260/555 A |
| 4,036,878 | 7/1977 | Kaasenbrood | 260/555 A |
| 4,053,507 | 10/1977 | Inoue | 564/71 |
| 4,082,797 | 4/1978 | Zardi | 260/555 A |
| 4,207,256 | 6/1980 | Inoue | 564/72 |

*Primary Examiner*—Brian E. Hearn
*Attorney, Agent, or Firm*—Morgan, Finnegan, Pine, Foley & Lee

[57] ABSTRACT

In a urea producing method by synthesis, the improvement which consists in feeding liquid ammonia in excess to the reactor so that a urea solution which contains ammonium carbamate is produced, the carbamate is decomposed in a high-pressure decomposer and the stripping agent is an inert, oxygen-containing gaseous stream, the carbamate decomposition products are sent to a high pressure condenser and ammonium carbamate is formed, whereafter the carbamate is separated from the inerts and the solution of urea coming from the high-pressure decomposer is fed to a medium-pressure decomposer which is fed through its bottom with inerts. The heat for operating the medium-pressure decomposer is a hot condensate from the high-pressure-decomposer-heating steam, and the products of decomposition of the carbamate coming from the medium-pressure decomposer are sent to a medium-pressure condenser together with a solution of ammonium carbonate coming from the low-pressure sections of the installation. Virtually pure, nonpolluting waters can be discharged from the installation.

2 Claims, 2 Drawing Figures

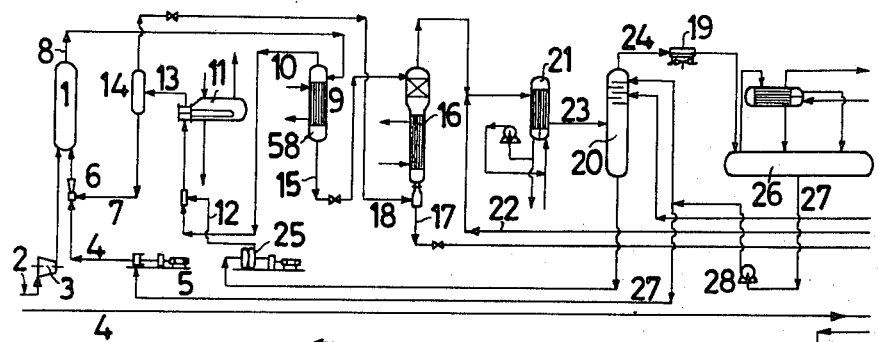
Fig.1a
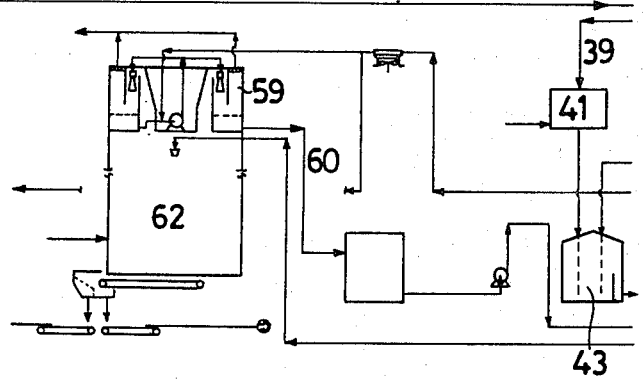
Fig.1b
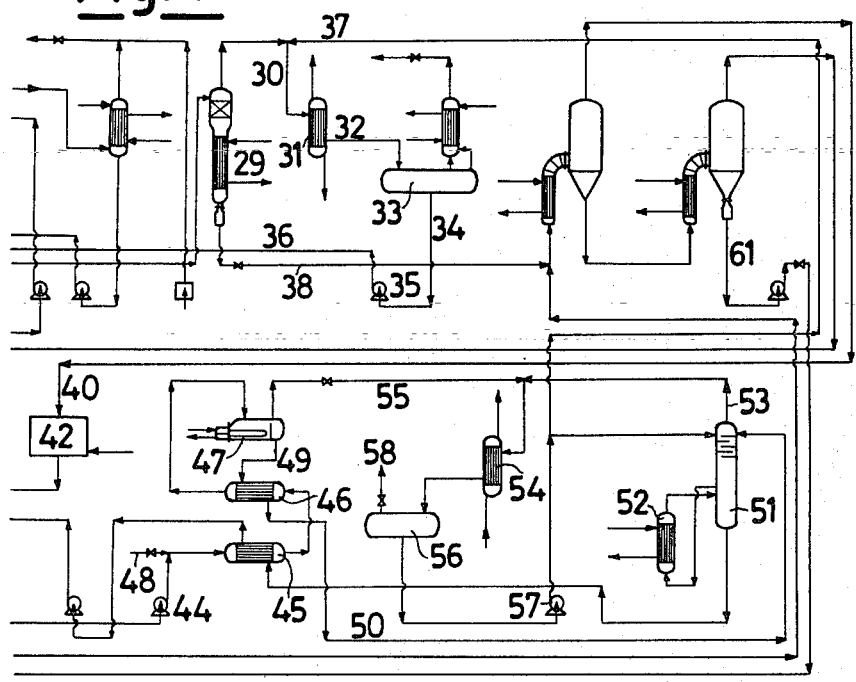

METHOD FOR THE PRODUCTION OF UREA AND PURIFICATION OF WATER

CROSS-REFERENCE TO RELATED APPLICATIONS

This application is a continuation of application Ser. No. 91,988, filed Nov. 7, 1979, the latter being a continuation of application Ser. No. 823,872, filed Aug. 11, 1977, both now abandoned.

This invention relates to a method for the production of urea and purification of water.

More particularly, the present invention relates to a method for the production of urea in which the power consumption is minimized and the water dumped from the installation does not present any pollution problems.

There are known in the art a number of methods for the synthesis of urea and among these a few which provide for an isobaric loop followed by a low-pressure section in which the urea solution is stripped by distillation of its ammonia and carbon dioxide contents which is in the form of ammonium carbamate and free ammonia.

Such conventional methods use, for the distillation of the urea solution coming from the high-pressure loop, costly live steam coming from the outside.

This fact, as it is apparent, is a considerable aggravating factor of the running costs of the installation.

In addition, the waters obtained in the methods according to the known art and which are sent to the sewers generally contain high urea values and high ammonia values, so that they are a considerable source of pollution.

All these shortcomings, and others, of the conventional urea plants are overcome by the method according to this invention.

The subject-matter of the present invention is a method for the production of urea and recovery of the water, which comprises the following steps:

a high-pressure urea-synthesizing reactor is fed with liquid ammonia in excess with respect to the stoichiometric quantity and with carbon dioxide, a urea solution being thus produced which contains ammonium carbamate.

ammonium carbamate is decomposed to $CO_2$ and $NH_3$ in a decomposer, substantially under the same pressure as in the synthesis (high-pressure decomposer) using as the stripper a stream of oxygen-containing inerts: the distiller is preferably of the film type, the products of the decomposition of the carbamate are fed to a condenser substantially under the same pressure of the synthesis run in which the formation of the ammonium carbamate takes place, in a separator the carbamate is separated from the inerts (which contain oxygen) which are introduced in the high-pressure decomposer as a stripping agent, the urea solution emerging from the high-pressure decomposer is then sent to a medium-pressure decomposer (generally a pressure of about 18 atmospheres is preferred) through the bottom of which are introduced, in counterflow relationship with respect to the solution, the inert gases which contain oxygen and which have been separated in the carbamate stripper aforementioned, the heat which is required for the operation of the medium-pressure decomposer is supplied by the hot condensate as obtained from the steam used for heating the high-pressure decomposer, the decomposition products of carbamate coming from the medium-pressure decomposer are sent to a medium-pressure condenser (the pressure therein is substantially the same as in the medium-pressure decomposer) together with a carbamate solution coming from the low-pressure portion of the installation.

It is important to observe that according to an aspect of the present invention, the medium-pressure condenser operates when it is empty of any liquid.

The condensate emerging from the medium-pressure condenser is sent to a rectification column from which ammonia is separated as a head product and a solution of ammonium carbonate is the tail product, said solution being recycled to the high-pressure carbamate condenser. The head $NH_2$ is recycled to the synthesis. The urea solution emerging from the bottom of the medium-pressure decomposer is sent to a low-pressure decomposer by operating in such a way as to obtain an aqueous solution of urea which still contains a consistent residue of ammonia (2 to 3% by weight) and of $CO_2$ (from 1% to 1.5%, by weight) and, on the head, there are vapors of $NH_3$ and $CO_2$ and $H_2O$ which are properly condensed in a low-pressure condenser which is also empty of any liquid and the condensate is recycled to the medium-pressure condenser aforementioned.

The urea solution as it emerges from the low-pressure decomposer is concentrated by evaporation of its water in a vacuum concentration system; the as-obtained urea (melted urea) is sent to prilling or to granulation whenever required, whereas the vapors (water, ammonia and carbon dioxide) are condensed and fed to the hydrolysis stage which is operated at a temperature of from 170° C. to 250° C., preferably at about 190° C., for a time of from 30 to 80 minutes, preferably from 40 to 60 minutes, in the presence of air.

The hydrolyzed solution is then sent to a rectification column to separate water as a tail product and, as a head product, upon condensation, an ammoniated solution, having a feeble concentration, of ammonium carbonate which is partly fed back as a reflux stream to the head of the rectification column and partly to the low-pressure condenser of the urea synthesis. The water is substantially pure.

It is worth noting that, quite apart from that which has been said in connection with the heat recovery as in the method of the present invention, that the oxygen-containing inerts are fed as stripping agents to the high-pressure decomposer, are then fed to the high-pressure condenser, are subsequently stripped of their carbamate and used anew as stripping agents in the medium-pressure decomposers, thus passivating all the high- and medium-pressure implementations. The inerts are then passed, in fact, to the medium-pressure condenser and the subsequent rectification column and are eventually separated from $NH_3$ which has been condensed and obtained as a head product.

This fact is an original aspect of the method according to this invention.

It is interesting to observe, moreover, that both the medium-pressure condenser and the low-pressure condenser are operated without any liquid in their interior and that both, apart the vapors coming from the condenser upstream thereof, are fed with solution of ammonium carbonate. The low-pressure condenser, above all, is fed with the solution of ammonium carbonate as obtained by condensation of the vapors as obtained in the hydrolyser and by condensation of the vapors coming from the column which rectifies the aqueous solution coming from the hydrolyser, whereas the medium-pressure condenser is fed with the condensate as obtained in the low-pressure condenser.

A critical condition is that the maximum weight ratio of the vapors to the solution(s) of carbonate fed to the two medium-and low-pressure condenser is not higher than 2.5 and that the minimum temperature of the coolant is 30° C.

It is interesting to observe that also the low-pressure condenser does not boost too much the decomposition reaction and causes to be left in the urea solution still a comparatively high amount of ammonia and carbon dioxide combined together in the carbamate form, and that the hydrolysis of the water which contains urea, ammonia and carbon dioxide is carried out in the presence of air.

BRIEF DESCRIPTION OF THE DRAWING

The foregoing and other aspects of the present invention will become more clearly apparent from the description of the accompanying drawing which illustrates a particular embodiment which does not limit the method according to this invention in any wise.

Lastly, it is interesting to observe that in the method according to the present invention the products dumped from the medium-pressure decomposer are condensed and separated in a liquid phase which comprises a solution of ammonium carbonate and a liquid phase which comprises substantially pure ammonia, rather than by a conventional rectification run as usually performed by the known art, by matching a medium-pressure condenser to a rectification column. By so doing, it is possible to operate the installation in a more versatile manner and it is concurrently possible to have the medium-pressure decomposer operated by the condensate as obtained in the high-pressure decomposer.

The method, the subject of the present invention, will be better understood from the attached FIGS. 1a and 1b, which show a preferred embodiment of the present invention but without limiting same, and which are to be read consecutively as shown in the assembly scheme also shown in the drawing.

The urea-synthesizing reactor, 1, operated at 150 kgs/sq. cm and 190° C., is fed with $CO_2$, 2, by the compressor, 3, and with $NH_3$, 4, by the pump 5. Ammonia, 4, prior to entering the reactor, 1, draws from the ejector, 6, the solution of recycled carbamate, 7. The urea solution, 8, from the reactor, 1, feeds the high-pressure decomposer or stripper, 9, which uses steam at 26 abs. atmospheres and 225° C.

The ammonia, carbon dioxide and water vapors, 10, emerging from the head of the stripper, 9, feed the carbamate condenser, 11, along with the solution of carbonate coming from the sections located downstream of the high-pressure loop now described, wherein they are exothermically condensed.

The heat evolved in the condenser 11 is removed by producing steam at 4.5 abs. atmosphere and at 147° C. Such steam is used up in the sections located downstream of the loop, as will be explained hereinafter.

The solution of condensed carbamate, 13, feeds the separator, 14, wherein the incondensable, oxygen-containing gases fed by 58 are separated and, from 14 the solution is recycled through 7 to the reactor 1 by means of the ejector 6.

The urea solution, 15, discharged from the bottom of the stripper 9 and sent to the subsequent handling in the downstream sections, has the following properties:
temperature—210° C.
pressure—150 kgs/sq.cm
$NH_3$—22% by weight
$CO_2$—5% by weight
urea—48% by weight
$H_2O$—25% by weight The solution, 15, feeds the medium-pressure decomposer, 16, which uses as a heating fluid the condensed steam coming from the stripper, 9, at 26 kgs/sq.cm and 225° C.

In the decomposer, 16, the steam condensates are cooled to 160° C. and the heat which has thus been yielded is supplied to the urea solution coming from 9 which is thus stripped of the major fraction of the ammonia and carbon dioxide contained therein.

The solution, 17, discharged from the bottom of 16 has the following properties:
temperature—155° C.
pressure—18 kgs/sq.cm
$NH_3$—6.5% by weight
$CO_2$—2.0% by weight
Urea—64.0% by weight
$H_2O$—27.5% by weight To the bottom of 16 are fed, in counterflow relationship with respect to the urea solution 15, the inert gases 18 coming from 14, with the advantage of unfolding a stripping effect and thus a low residual contents of $NH_3$ and $CO_2$ in the solution, even operating at the comparatively low temperatures (155° C.) to which one is compelled to work when using as a heating means the condensate instead of the live steam and with the further advantage of passivating the decomposer 16 inasmuch as oxygen is present in the inert gas stream.

The pressure in 16 and thus also the temperature at which the urea solution must be heated in order that a maximum distillation of ammonia and carbon dioxide may be obtained is bound to the system of recovery and recycling of the vapors produced at 16.

It is advisable to work at the lowest possible pressure, but the bottom value of the pressure is determined by the temperature of the cooling means employed in the head condenser 19 of the distillation column 20. The vapors coming from the head of 16 and composed by ammonia, carbon dioxide and $H_2O$ feed the condenser 21, the latter working at 18 kgs/sq.cm and 70° C.

In addition to the condenser 21 is fed the diluted solution, 22, of carbonate coming from the low-pressure recycling section. The uncondensed coming from 21 and composed by inert gases, ammonia, and carbon dioxide and residual water along with the condensate feed through 23 the rectification column 20 in which, by a head reflux of pure ammonia, the complete absorption of $CO_2$ and $H_2O$ is obtained, pure ammonia being concurrently obtained as the head product, at 24.

From the bottom of the column 20 the carbonate solution, 12, is dumped, which is fed back to the carbamate condenser, 11, of the high-pressure loop by means of the pump 25.

The carbonate solution has the following properties:
Temperature—65° C.
pressure—18 kgs/sq.cm
$NH_3$—45.5% by weight
$CO_2$—18.5% by weight
$H_2O$—36.0% by weight From the head to the column 20, one discharge, through the main 24:
  pure gaseous ammonia (a few parts per million of $CO_2$ and $H_2O$ as residues) and
  inert gases,
at a temperature of 43° C. and a pressure of 17.5 kgs/sq.cm.

The gas discharged from 20 feeds the condenser 19 wherein the major fraction of ammonia is condensed and is collected in the storage tank 26 together with the fresh ammonia 4 to be fed to the installation. The inerts emerge from 26. From the tank 26 the liquid ammonia is, for the major aliquot, sent to the reactor 1 through 27 and the pumps 28 and 5 and is partly sent to the head of the column 20 through the pump 28. As outlined above, it is imperative that the decomposer 16 is operated at the lowest possible pressure and it has been found, according to the invention, that it is necessary that the condenser 21 works without any liquid in its interior.

It was surmised, according to that which was customary, that it were impossible to achieve such a result, that is to work with empty carbamate condensers, and the condenser of the vapors of ammonia, carbon dioxide and water usually work full of the processing liquor (solution of carbamate and carbonate) to make homogeneous the solution and to prevent crystallization phenomena and consequential cloggings and plant stoppage.

The admixtures of vapors of ammonia, carbon dioxide and water by being fractionally condensed usually originate, in the liquidless processing condensers (empty), areas with a high concentration of carbon dioxide and thus crystallization problems.

This is prevented in the method according to the present invention with the following conditions:
  a maximum weight ratio of the vapors to the diluted carbonate solution not higher than 2.5;
  a minimum temperature of the coolant medium of 30° C.

The stream 17 coming from the decomposer 16 is fed to a decomposer 29 which works under a pressure of about 4.5 atmospheres at a temperature of about 138° C. (bottom temperature).

The decomposer 29 aforesaid operates in such a way as to maintain a comparatively high residual contents of ammonia and carbon dioxide in the solution of urea, with the following advantages:

(1) a low temperature of the urea solution which makes possible an economically acceptable use of steam at 4.5 atmospheres (147° C.), (2) the presence of ammonia in the solution of urea sent to the final treatment (concentration in a vacuo and crystallization), which minimizes the urea decomposition phenomena.

The urea solution at the outlet of the decomposer 29 is composed by:
  $NH_3$—2% by weight
  $CO_2$—1% by weight
  Urea—71% by weight
  $H_2O$—26% by weight In the conventional procedure in which, in this stage, a very accurate purification of the urea solution is carried out ($NH_3$ less than 1%) it is necessary to operate, the pressure being the same, at a temperature higher than 150° C., thus rendering economically unacceptable the use of low-pressure steam coming from the carbamate condenser. The vapors of ammonia, carbon dioxide and water coming from the head of the decomposer 29 (stream 30) are totally condensed in the condenser 31. The carbonate solution thus obtained is sent via 32 to the tank 33 and recycled via the pipings 34 and 36 and the pump 35 to the condenser 21. Also in this latter section of the installation, it is vital that the working pressure of the decomposer 29 be the lowest possible since it is determined by the temperature of the coolant medium in the condenser 31 and the minimum temperature which can be attained in the condenser 31 without having to cope with crystallization phenomena.

In this case, too, the condenser 31 is empty and the diluted ammoniated solution 37 emerging from the sewage water treatment section is fed to the condenser 31 and encourages the total condensation of the vapors. The urea solution, 38, coming from 29 is fed to the final vacuum concentration treatment (in the specific example shown in the drawing) in order to obtain waterless urea.

The water vapors, polluted with ammonia, carbon dioxide and urea, are introduced, via the lines 39 and 40, into the vacuum section 41, 42 wherein they are condensed and are the sewage water of the installation, which is collected in the vessel 43 and properly treated as will be described hereinafter.

The discharge water coming from 43 has the following composition:
  $NH_3$—4 to 5% by weight
  $CO_2$—1.5 to 2.5% by weight
  urea—0.5 to 2.0% by weight
  water—balance to 100%.

Such a water, through the pump 44 is sent, after having been heated in the heat-exchangers 45 and 46, to the hydrolyser 47 which operates at least 180° C. and 18 atmospheres.

In the hydrolyser 47 there is air blown from 48, continually removed from 47 and used to the purpose of reducing the partial pressure of ammonia and carbon dioxide so as to encourage hydrolysis. The aqueous solution remains in the hydrolyser 47 for 40–60 mins. at 169° C. and the virtually total hydrolysis of the urea which is present is obtained (the residual contents is less than 200 parts per million).

The aqueous solution in the hydrolyser is heated with steam in the conventional manner.

The hydrolyzed solution emerges from the hydrolyser 47 via 49 and preheats in the exchanger 46 the solution to be fed to the hydrolyser up to about 173° C. The solution is then fed through 50 to the rectification column 51 where the ammonia and carbon dioxide contained therein are removed. The column 51 has a bottom reboiler 52 which is heated by steam. The head vapors 53 formed by a mixture of ammonia, carbon dioxide and water are sent to a condenser 54 where they are also reached by the vapors 55 coming from the hydrolyser 47. The water which has been treated and emerges from the bottom of 51 has the following residual impurity contents:
  $NH_3$—from 25 to 50 parts per million
  Urea—from 100 to 200 parts per million It preheates the water to be sent to the hydrolyser 47 in the exchanger 45. The ammoniated solution obtained in 54 is collected in the tank 56 and therefrom, via the pump 57 is partly refluxed to the head of the column 51 and partly to the condenser 31. Air is vented from 56 via the pipe 58.

In the example shown in the drawing, the water coming from 51 after the recovery of heat as aforesaid is sent to the apparatus for the recovery of the urea dust 59 and the aqueous solution of urea thus obtained, 60, is sent to the recovery of urea in the vacuum concentration stage.

The melted urea 61 is sent from the concentrators to the prilling tower 62. If the dusts are not recovered, the water coming from 51 is dumped.

We claim:

1. In a method for the production of urea and purification of the waters obtained therefrom, comprising feeding to a synthesizing reactor of urea under high pressure liquid ammonia in excess over the stoichiometric amount and carbon dioxide so as to produce a urea solution containing ammonium carbamate, decomposing in a decomposer substantially under the same pressure as the synthesizing pressure (high-pressure decomposer) the carbamate contained in the solution of urea into ammonia and carbon dioxide by using an inert stripping agent which contains oxygen, condensing in a condenser substantially under the same pressure as the synthesis (high-pressure condenser) said ammonia and carbon dioxide and recycling the condensate to the synthesis, discharging from the decomposer a solution of urea which still contains carbamate and dissolved ammonia, sending such solution of urea from the high-pressure decomposer to a medium-pressure decomposer having a lower pressure than that in the high pressure decomposer, the gaseous products discharged from the latter conveyed to a medium-pressure condenser wherein said products are separated into a liquid phase formed of ammonium carbonate and a liquid phase formed of substantially pure ammonia, said liquid phase composed of ammonium carbonate being recycled to the high-pressure condenser and said liquid phase composed of substantially pure ammonia being sent to the synthesis, sending the urea solution emerging from the medium-pressure decomposer to a low-pressure decomposer having a lower pressure than that in the medium pressure decomposer from which there are obtained as head product ammonia, carbon dioxide and water which are condensed in a low-pressure condenser at a pressure no greater than the pressure in the low pressure decomposer, and as tail product a solution of urea which still contains ammonia and carbon dioxide, sending the aqueous urea solution emerging from the low-pressure decomposer to a vacuum concentrator to obtain melted urea and water vapor with ammonia and carbon dioxide which are condensed, the improvements which comprise operating said medium-pressure condenser and low-pressure condenser free of any liquid, both said condensers being fed with the vapors of the decomposers upstream thereof and ammonium carbonate solutions obtained from said low pressure condenser, and both said condensers are operated at the same pressure as that in the corresponding preceding decomposer, wherein the maximum weight ratio of said vapors to said carbonate solution does not exceed 2.5 and the coolant medium has a minimum temperature of 30° C.

2. In a method for the production of urea and purification of the waters obtained therefrom, comprising feeding to a synthesizing reactor of urea under high pressure liquid ammonia in excess over the stoichiometric amount and carbon dioxide so as to produce a urea solution containing ammonium carbamate, decomposing in a decomposer substantially under the same pressure as the synthesizing pressure (high-pressure decomposer) the carbamate contained in the solution of urea into ammonia and carbon dioxide by using an inert stripping agent which contains oxygen, condensing in a condenser substantially under the same pressure as the synthesis (high-pressure condenser) said ammonia and carbon dioxide and recycling the condensate to the synthesis, discharging from the decomposer a solution of urea which still contains carbamate and dissolved ammonia, sending such solution of urea from the high-pressure decomposer to a medium-pressure decomposer having a lower pressure than that in the high pressure decomposer, the gaseous products discharged from the latter conveyed to a medium-pressure condenser wherein said products are separated into a liquid phase formed of ammonium carbonate and a liquid phase formed of substantially pure ammonia, said liquid phase composed of ammonium carbonate being recycled to the high-pressure condenser and said liquid phase composed of substantially pure ammonia being sent to the synthesis, sending the urea solution emerging from the medium-pressure decomposer to a low-pressure decomposer having a lower pressure than that in the medium pressure decomposer from which there are obtained as head product ammonia, carbon dioxide and water which are condensed in a low-pressure condenser at a pressure no greater than the pressure in the low pressure decomposer, and as tail product a solution of urea which still contains ammonia and carbon dioxide, sending the aqueous urea solution emerging from the low-pressure decomposer to a vacuum concentrator to obtain melted urea and water vapor with ammonia and carbon dioxide which are condensed, the improvements which comprise:

(a) separating the gaseous products discharged from the low-pressure decomposer by condensing them in a condenser substantially under the same pressure as the medium-pressure decomposer, the liquid product thus obtained and the residues composed of inerts, ammonia, $CO_2$ and residual water fed to a rectification column from which there is obtained as the head product substantially pure ammonia and as a tail product a solution of ammonium carbonate;

(b) separating the oxygen-containing inerts used as the stripping agent in the high-pressure decomposer from the carbamate which has been condensed under high pressure in a separator and then using them as a stripping agent in the medium-pressure decomposer wherefrom they are passed to the medium-pressure condenser and then to the rectification column to be eventually separated from the condensed ammonia produced as the head product;

(c) obtaining the heat necessary for operating the medium-pressure decomposer by condensing the steam used for operating the high-pressure decomposer;

(d) operating said medium-pressure condenser and low-pressure condenser free of any liquid, both said condensers being fed with the vapors of the decomposers upstream thereof and ammonium carbonate solutions obtained from said low pressure condenser, and both said condensers are operated at the same pressure as that in the corresponding preceding decomposer, wherein the maximum weight ratio of said vapors to said carbonate solution does not exceed 2.5 and the coolant medium has a minimum temperature of 30° C.;

(e) maintaining the aqueous urea solution at the outlet of the low-pressure decomposer at a concentration of from 2% to 3% by weight of ammonia and from 1% to 1.5% by weight of carbon dioxide; and (f) subjecting the condensate composed of water, ammonia and carbon dioxide obtained by condensation of the vapors coming from the vacuum concentrator to hydrolysis and subsequent separation of the decomposition products, substantially pure water being obtained and a solution of ammonium carbonate which is recycled to either, or to both, the medium- or low-pressure condensers.

* * * * *